United States Patent [19]

Waldner

[11] 4,429,424
[45] Feb. 7, 1984

[54] OSTOMY COLLECTOR-ORGANIZER DEVICE

[76] Inventor: Nelson D. Waldner, 8782 Sea Spray Dr., Huntington Beach, Calif. 92646

[21] Appl. No.: 391,532

[22] Filed: Jun. 24, 1982

[51] Int. Cl.³ .............................................. A47K 11/00
[52] U.S. Cl. .......................................... 4/479; 4/449; 604/317
[58] Field of Search ................... 4/449, 458, 457, 479, 4/480, 661, 274, 258; 128/760, 761, 767; 604/317, 328, 321, 332-345; D24/57-59

[56] References Cited

U.S. PATENT DOCUMENTS

| | | | |
|---|---|---|---|
| 2,471,201 | 5/1949 | Deardorff | 4/479 |
| 2,639,711 | 5/1953 | Smith et al. | 604/334 |
| 2,664,573 | 1/1954 | Taylor | 4/661 |
| 3,929,412 | 12/1975 | Villari | 128/760 |

Primary Examiner—Stephen Marcus
Assistant Examiner—Kenneth S. Putnam
Attorney, Agent, or Firm—Willie Krawitz

[57] ABSTRACT

A portable, stable device for collecting body waste from an ostomy collector bag worn by individuals having an ileostomy or similar condition, is provided. The device is compact and organized into various compartments containing items such as napkins, tissues, discharge receptacles, covers, receptacle liners, etc. The device also provides a stable platform for the discharge receptacle, and is further stabilized between the user's legs; this arrangement frees the user's hands to manipulate the ostomy equipment during the draining procedure. The receptacle containing body waste may be stored temporarily, and then flushed to waste.

5 Claims, 4 Drawing Figures

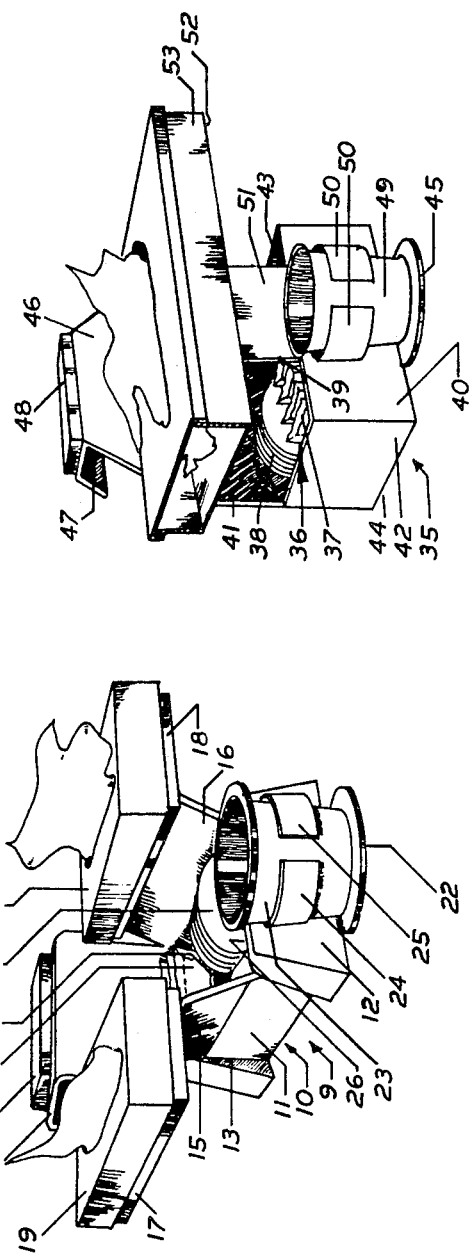

OSTOMY COLLECTOR-ORGANIZER DEVICE

BACKGROUND OF THE INVENTION

This invention relates to a stable, portable, body waste collection device for use by persons having an ostomy or similar condition. The ostomy is a surgically created opening in the abdomen, the end of the intestine being extended through this opening; a person who has an ostomy is known as an ostomate. Intestinal contents or urinary diversion is expelled from the body through this opening and into a drainable collector bag that is worn by the Ostomate. When the bag is filled, the contents are discharged usually into a toilet.

The problem with this arrangement is that the Ostomate does not have any control of the time or quantity of the contents being expelled from the body into the collection bag. Hence, it may be necessary to drain the bag at times that are unexpected and not convenient, or without the user having access to toilet facilities.

Frequently, it is inconvenient to drain the bag, particularly in public rest rooms that are either unsanitary or not totally private, or in toilet facilities that are not available for public use.

In many cases, the Ostomate would prefer to drain or discharge the contents of the collector bag into a receptacle just prior to entering a public building to avoid wearing a conspicuously filled bag. However, this can be quite inconvenient insofar as privacy and actual use are concerned.

One problem when using a discharge receptacle is that it is fairly conspicuous; also, it is not very stable. Usually, it is quite difficult to manipulate the ostomy equipment simultaneously with the discharge receptacle. It would be desirable to provide a simplified and combined organizer and holder means during use of discharge receptacles by persons having an ostomy condition, and the like. Such an organizer-holder should have relatively few or no moving parts.

Preferably, such a device would provide a stable platform that can support the discharge receptacle and also function as a storage and organizer for items required in the collection of body waste.

Also, it would be desirable to provide a device which would allow the user to drain the collector bag whenever necessary or desired within the privacy of any closed quarters, automobile or van. There is also desired a device that is reasonably inconspicuous when carried in say, an automobile, and where the collector components appear relatively innocuous, while still providing the sanitary conditions required for proper ostomy care.

THE INVENTION

According to the invention, there is provided a portable, collector-organizer device for receiving body waste that has been evacuated into a collector bag worn by persons having an ileostomy condition, a urostomy, and the like.

The device of this invention includes compartments for storing tissues, wipe napkins, discharge receptacles, lids, receptacle liners, etc. The device also provides the dual function of supporting a disposable discharge receptacle during use in a convenient manner.

Structurally, the device comprises a compartmented container having closed sides, forward and rear end walls, bottom, and an open top for ease of access. Rearwardly and centrally of the device is a pad that supports a body waste discharge receptacle. The forward end of the device defines an end wall that may be configured for hanging from a support. Upwardly extending members from the sidewalls support twin platforms that rest on the user's legs during use. The device may be stabilized between the user's legs, by means of the platform and by pressure on the forward wall. Following use, the discharge receptacle is closed with a lid and disposed to waste; if desired, it may be stored temporarily prior to disposal.

BRIEF DESCRIPTION OF THE DRAWINGS

FIGS. 1 and 2 are front elevation perspective views of the collector-organizer device of this invention;

DESCRIPTION OF THE PREFERRED EMBODIMENTS

Figure 3:
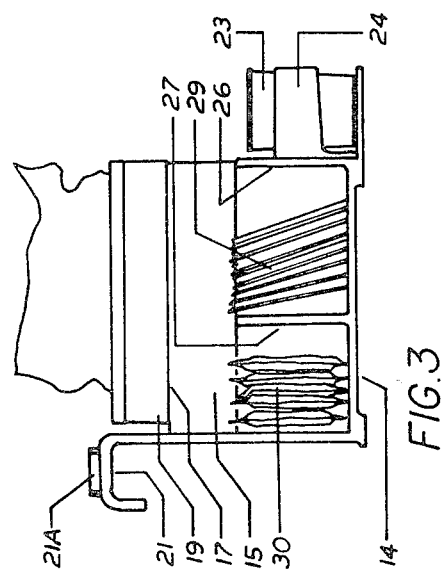
FIG. 3 is a side elevation view, partly external, and partly in section showing the compartments containing items of use, and the discharge collector support; and, FIG. 4 is a side elevation view, partly in section, showing the collector-organizer device in operation.

One type of a collector-organizer device 9 of this invention is shown in FIG. 1, and is suitable for bedridden persons, and the like. The device comprises a container compartment portion 10 having sidewalls, one sidewall 11 being shown, a front wall 12, a rear wall 13, and a bottom 14 (FIG. 3). Flanges 15, 16 slope upwardly from the upper edges of the sidewalls and form flat platforms 17, 18 that support tissue holders 19, 20. The rear wall 14 extends upwardly to form a U-shaped hanger portion 21 for the device. The hanger may also function to be grasped by the user for steadying the device. If desired, the hanger portion 21 can be reinforced by a thick segment 21A so that it may be used as a closure tray during the draining process, or to hang in an automobile, or be used as a carrying handle.

A support pad 22 is positioned at the front end, and centrally of the device, and supports a discharge receptacle 23 for receiving body waste. Flexible bands 24, 25 secure the receptacle in place, and these bands may be flexed outwardly so that the receptacle can be inserted or removed. Alternatively, the receptacle can be placed on the pad simply by pressing it downwardly through the inwardly directed force of the bands.

Compartments 26, 27 are provided in the container compartment portion 10 for storing lids 29, towelettes 30, discharge receptacles (not shown), etc. The device 9 can be injection molded readily from suitable plastics; this reduces the cost and enables the device to be washed and sterilized easily.

FIG. 2 illustrates a somewhat smaller collector-organizer 35 compared to that shown in FIG. 2; it is suitable for use on short trips, pediatrics, etc. The collector-organizer includes a container portion 36 having various compartments for towelettes 37, lids 38 and receptacles 39, respectively.

The container portion 36 has a front wall 40, rear wall 41, side walls 42, 43 and a bottom 44. A centrally located support pad 45 is provided forwardly of the collector. The rear wall 41 includes an upstanding portion 46 that forms a U-shaped hanger portion 47, and a reinforcement element 48 along an upper edge of the hanger portion. The reinforcement element also serves as a tray for a closure during the draining procedure and can be used to hang in an automobile or as a carrying handle. A discharge receptacle 49 is supported on the pad 45 and is secured in place by flexible bands 50; when the bands are flexed outwardly, the discharge receptacle can be removed.

Since the support pad 45 and discharge receptacle 49 are located centrally of the collector-organizer 35, the discharge container will be relatively stable despite motion of the device, say in a moving vehicle, plane, etc. An upstanding element 51 is attached to the front wall 40 and mounts a horizontal stand 52 that rests on the user's legs; the stand also is adapted to support a tissue holder 53.

Figure 4:
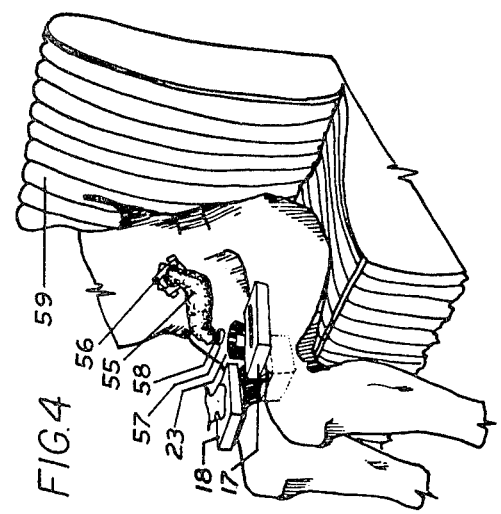

The device 9 is shown in operation in FIG. 4 in conjunction with an ostomy collector bag 55 that is worn over a surgical opening. The bag is attached to the body by an ostomy appliance (not shown), and also a tape 56. The bag 55 collects body waste being expelled from the intestine through the surgical opening and into the bag. A drain opening 57 in the bottom of the bag is controlled by a pouch closure 58; when the discharge collector bag 55 becomes filled, the user simply opens the closure and drains the bag.

From the standpoint of convenience, the collector-organizer device is employed by the user when seated, and this enables the device to be positioned on say a car seat 59 and stabilized between the user's legs and by the platforms 17, 18 resting on the user's legs. Typically, the discharge receptacle has about a 350 c.c. capacity and is either leak proof, or it may employ a thin, biodegradable liner, not shown. Alternatively, if the liner is made of a thicker material, it may be used as the discharge receptacle itself.

When the collector bag 55 has been emptied into the discharge receptacle 23, the drain opening is wiped clean using the tissues and towelettes, and the receptacle is then closed with a lid 28. The receptacle may then be removed from the device, temporarily stored, and is eventually disposed to waste. If desired, deodorants, germicides, etc., may be added to the receptacle to increase the storage life of the discharged material.

The organizer-collector device of this invention also has particular use for wheelchair or bedridden individuals having an ileostomy, urostomy, or similar condition and who are unable to attend the bathroom without assistance to carry out the draining procedure.

I claim:

1. A portable, stable, collector-organizer device for receiving body waste through the drain opening of an ostomy collector bag, comprising:
  a. an open container having compartments for storing receptacles adapted to receive and collect body waste from the drain opening, lids for closing the receptacles, and wiping towels and tissues for cleaning and wiping the drain opening;
  b. front, rear and side walls enclosing the container;
  c. a support pad positioned forwardly of the front wall and centrally of the device, the pad being adapted to support the receptacle;
  d. means for releasably securing the receptacle on the pad; and,
  e. upwardly extending arms from the walls terminating in horizontal support platforms;
  the device being adapted, when in use, to be stabilized and secured: i. along the sidewalls between a user's legs when seated; and, ii. by the platforms resting upon the top of the user's legs; whereby, the user is enabled to insert the drain opening of the ostomy collector bag into the discharge receptacle and thereby drain the contents of the ostomy collector bag into the receptacle.

2. The device of claim 1, in which the upwardly extending arms are attached to the sidewalls.

3. The device of claim 1, in which the upwardly extending arm is attached to the rear wall.

4. The device of claims 2 or 3, in which an upper extension from the rear wall terminates in a hanger and support ledge.

5. The device of claim 1, in which flexible clasp means are provided for releasably securing the receptacle.

* * * * *